(12) United States Patent
Lin (10) Patent No.: US 6,814,717 B2
(45) Date of Patent: Nov. 9, 2004

(54) PROTECTING CAP STRUCTURE FOR THE NEEDLE OF A SYRINGE

(75) Inventor: Bih-Chern Lin, Taichung (TW)

(73) Assignee: Future Top Medical Environmental Technic Co., Ltd., Taipei (TW)

( * ) Notice: Subject to any disclaimer, the term of this patent is extended or adjusted under 35 U.S.C. 154(b) by 0 days.

(21) Appl. No.: 10/050,565

(22) Filed: Jan. 18, 2002

(65) Prior Publication Data

US 2003/0139704 A1 Jul. 24, 2003

(51) Int. Cl.⁷ ............................ A61M 5/32; A61M 5/00; B65D 83/10
(52) U.S. Cl. ...................... 604/192; 604/198; 604/263; 604/110; 604/197; 206/364
(58) Field of Search ................................. 604/192–198, 604/110, 263, 187; 206/364–368; 600/578; 128/919

(56) References Cited

U.S. PATENT DOCUMENTS

| | | | | |
|---|---|---|---|---|
| 4,838,871 A | * | 6/1989 | Luther | 604/192 |
| 5,011,475 A | * | 4/1991 | Olson | 604/192 |
| 5,269,765 A | * | 12/1993 | Kuracina | 604/192 |
| 6,171,284 B1 | * | 1/2001 | Kao et al. | 604/192 |
| 6,635,032 B2 | * | 10/2003 | Ward, Jr. | 604/192 |

* cited by examiner

*Primary Examiner*—Brian L. Casler
*Assistant Examiner*—Roz Maiorino
(74) *Attorney, Agent, or Firm*—Troxell Law Office PLLC (57) ABSTRACT

A protecting cap structure for the needle of a syringe, wherein, the structure is provided with a protecting sleeve having a receiving space for receiving a needle. The protecting sleeve is comprised of a foldable cover and a cylindrical extendible member connected with each other; the cylindrical extendible member is a hollow cylinder, the shank of the cylindrical extendible member has a compression portion; a pair of foldable portions are provided in neighboring to the compression portion; the foldable cover is in the shape of a semi-cylinder, one end of the foldable cover is connected with the cylindrical extendible member, in order that when the cover is folded to close, it cooperates with the cylindrical extendible member to envelop and fast envelop the needle to prevent the needle from accident stabbing.

4 Claims, 8 Drawing Sheets

PROTECTING CAP STRUCTURE FOR THE NEEDLE OF A SYRINGE

BACKGROUND OF THE INVENTION

1. Field of the Invention

The present invention is related to a protecting cap structure for the needle of a syringe; and is especially to a device with an cylindrical extendible member and a foldable cover connected with each other, the device can fast obscure the needle to prevent it from accident stabbing, thus it is suitable to be a protecting cap structure or the like.

2. Description of the Prior Art

Since syringes were widely used, needles for syringes have been frequently inadvertently used to accidentally stab medical workers. Therefore, the modes of storage of needles have been always highly thought of; and various protecting structures for the needles of syringes have been developed.

However, most conventional protecting structures for the needles of syringes have a sleeve for each needle generally in the shape of an elongate cylinder having a receiving chamber with a predetermined longitudinal depth for insertion therein of the needle of the corresponding syringe; the elongate cylinder of the protecting sleeve is provided on the external surface thereof with a protective pick-up portion extending a predetermined length outwardly to allow a user to pick up with fingers, the protective pick-up portion has a predetermined distance from the external surface of the syringe to provide a safe distance when in picking up; however, with this safe distance from the syringe during picking up the protective pick-up portion by the user, the syringe still needs to be aligned with the sleeve for the needle for inserting after use to make obscuring of the needle. While in the procedure from taking the sleeve to slipping the needle of the syringe into the sleeve, it is still probable that cases of accident stabbing by the needle may occur; and more, after slipping connecting of the sleeve with the syringe, there is no stable connection between the two, this tends to have the chance that the sleeve drops; therefore, such conventional protecting structures still have the defect of inadvertence in using the needle to accidentally stab a person.

SUMMARY OF THE INVENTION

The primary object of the present invention is to provide a protecting cap structure for the needle of a syringe, wherein, by providing a device with an cylindrical extendible member and a foldable cover connected with each other, the present invention can envelop the needle and prevent the needle from accident stabbing and thereby can increase practicality as well as safety of the present invention.

Another object of the present invention is to provide a protecting cap structure for the needle of a syringe, wherein, the cylindrical extendible member can be compressed to fixedly engage with the cover for mutual positioning, so that medicine can be injected conveniently, and convenience as well as practicality of the present invention can be increased.

To get the above object, the present invention is provided with a protecting sleeve having a receiving space for receiving a needle; the protecting sleeve is comprised of a foldable cover and a cylindrical extendible member connected with each other. The cylindrical extendible member is a hollow cylinder, the shank thereof has a compression portion with a suitable length; a foldable portion is provided in neighboring to the compression portion. The cover is in the shape of a semi-cylinder, one end of the cover is connected with the cylindrical extendible member in order to combine with the cylindrical extendible member when the cover is folded to close to thereby envelop the needle. And thereby, the needle is fast obscured to prevent it from accident stabbing, and practicality as well as safety of the present invention can be increased.

The present invention will be apparent in its features and structure after reading the detailed description of the preferred embodiment thereof in reference to the accompanying drawings.

DETAILED DESCRIPTION OF THE PREFERRED EMBODIMENT

Referring to FIGS. 1–4, the protecting cap structure for the needle of a syringe in present invention is provided with a protecting sleeve 1 having a receiving space for receiving a needle 21; the protecting sleeve 1 is connected with a syringe 2.

The protecting sleeve 1 is comprised of a foldable cover 11 and a cylindrical extendible member 12 connected with each other.

The cylindrical extendible member 12 is a hollow cylinder, the shank thereof has a compression portion 121 with a suitable length; a pair mutually opposite foldable portions 122 slightly bending outwardly in favor of folding are provided in neighboring to the compression portion 121. The cylindrical extendible member 12 has on the bottom wall portion thereof a protrusion 123, and a corresponding foldable extension section 128 is provided also on the bottom wall portion of the cylindrical extendible member 12, the foldable extension section 128 is provided with a through hole 124 for engagement; a hooking strip 125 is provided on the bottom wall portion of the cylindrical extendible member 12. And a hole 126 is provided centrally on the top of the cylindrical extendible member 12 which has a annular flange 127 on this top.

The foldable cover 11 is in the shape of a semi-cylinder, one end of the cover 11 is connected with the cylindrical extendible member 12 (or is integrally formed with the latter), the inner diameter of the cover 11 is slightly larger than the external diameter of the cylindrical extendible member 12; the cover 11 is provided on the two sides thereof each with an engaging notch 112, and is provided on the wall thereof with an engaging hole 111; so that when the cover 11 is folded to close, it can be engaged with the hooking strip 125 provided on the bottom wall portion of the cylindrical extendible member 12.

With the above elements constructing the protecting cap structure for the needle of a syringe, referring to FIGS. 2a–4, the present invention is characterized by that, the foldable cover 11 extending and provided beside the cylindrical extendible member 12 can be folded to close up; and by appropriate rotating of the foldable cover 11, the engaging hole 111 on the wall of the foldable cover 11 engages with the hooking strip 125 provided on the bottom wall portion of the cylindrical extendible member 12 to thereby prevent the cylindrical extendible member 12 from being compressed. In this way, the needle 21 in the protecting sleeve 1 is enveloped in the latter and is prevented from exposing to thereby prevent accident stabbing of the needle 21. When the engaging hole 111 on the wall of the foldable cover 11 is released from the hooking strip 125 provided on the bottom wall portion of the cylindrical extendible member 12, the bottom end of the shank of the cylindrical extendible member 12 is engaged with the front end of a protruding portion on the root of the needle 21, and the protrusion 123 on the bottom wall portion of the cylindrical extendible member 12 engages the needle 21 together with the through hole 124 on the foldable extension section 128 to make firm connection of the protecting sleeve 1 with the syringe 2. When the cylindrical extendible member 12 is compressed downwards, the two foldable portions 122 provided adjacent to the corresponding compression portion 121 are bent to collapse, so that they can be engaged into the engaging notches 112 provided on the two sides of the cover 11. Thereby, the compression portion 121 of the cylindrical extendible member 12 being compressed downwards and the corresponding engaging notches 112 can not elastically move back, this allows practicing of medicine injection. After injection, engagement between the two foldable portions 122 and the engaging notches 112 can be released to make the compression portion 121 of the cylindrical extendible member 12 being compressed downwards and the corresponding engaging notches 112 move back by elastic restoration, the needle 21 thereby is enveloped in the protecting sleeve 1 and is prevented from exposing and to prevent accident stabbing thereof. Thus the present invention can envelop the needle and can prevent the needle from accident stabbing; and thereby can increase practicality as well as safety thereof. In this way the protecting cap structure for the needle of the syringe is completed.

Figure 1:
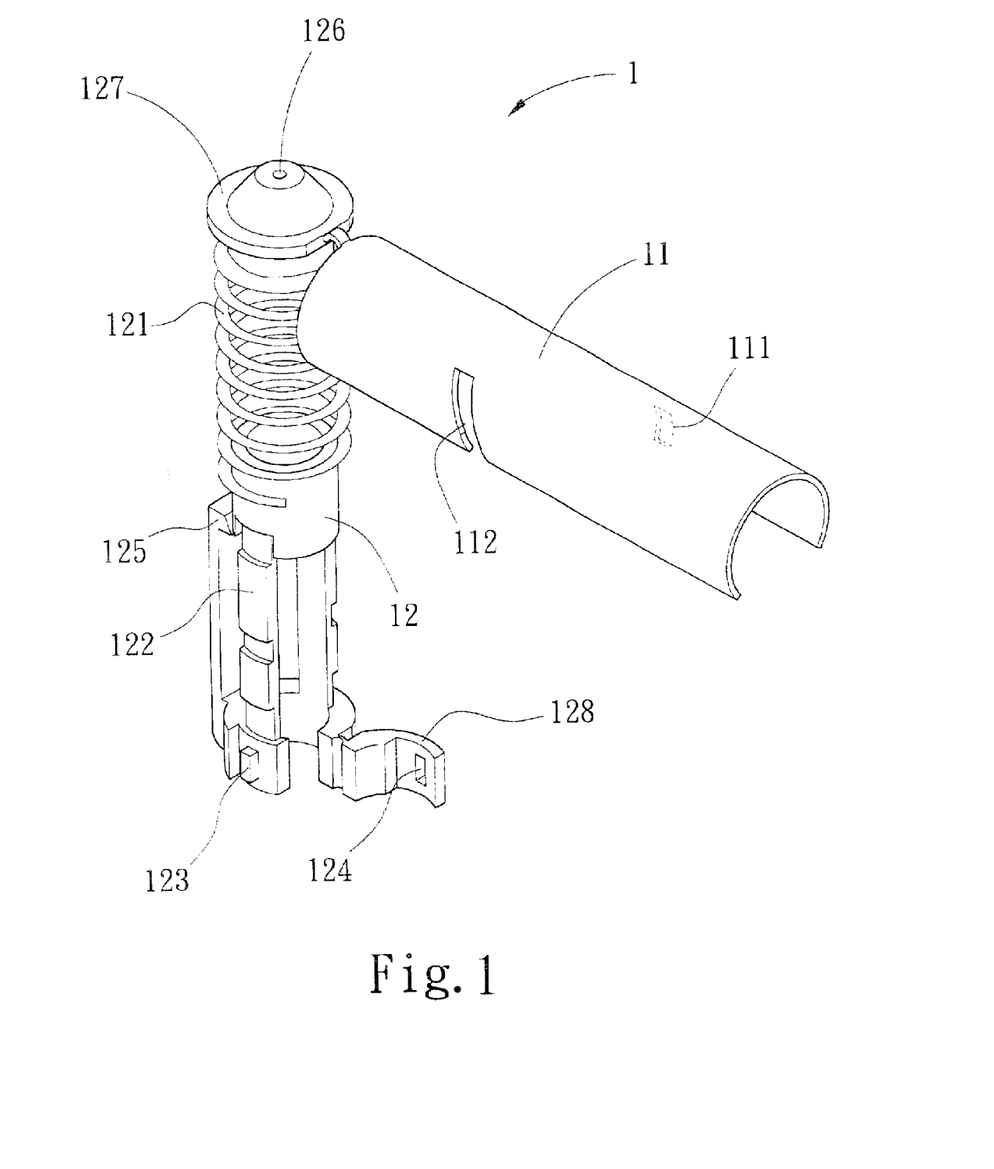
FIG. 1 is a perspective view of the protecting sleeve of an embodiment of the present invention.
Figure 2A:
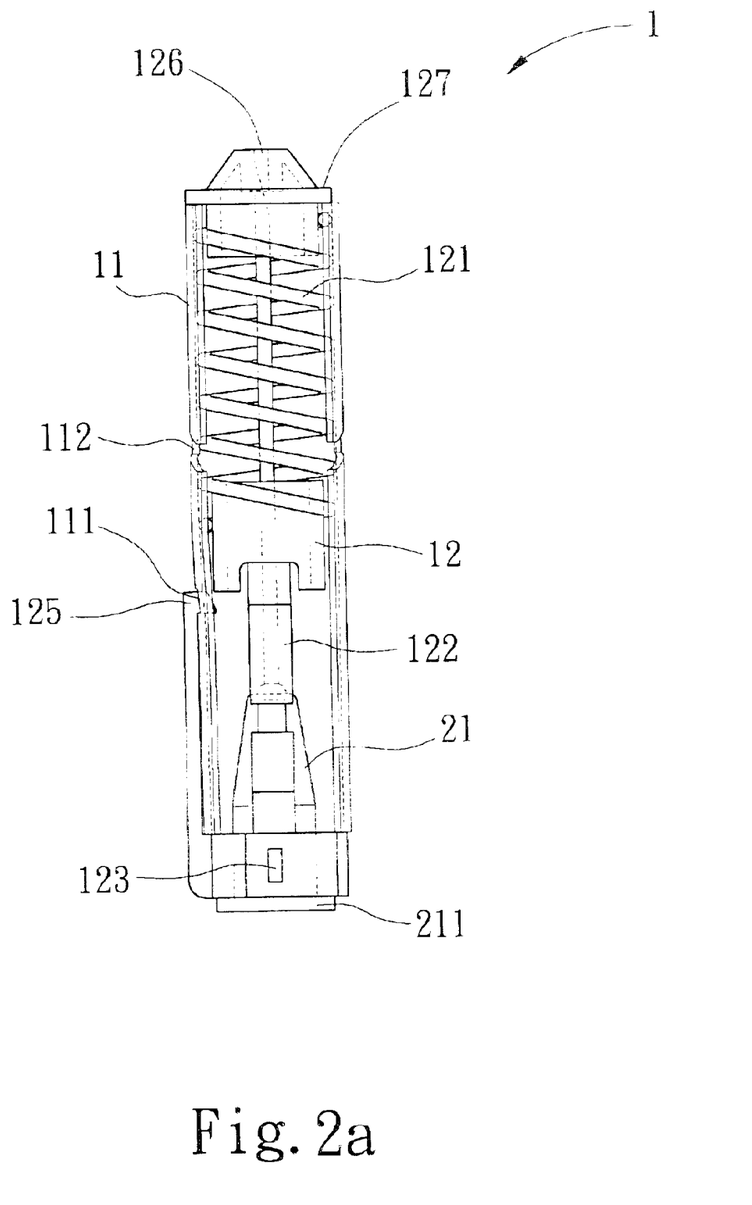
FIG. 2a is a schematic view of the closed protecting sleeve of the embodiment of the present invention.
Figure 2B:
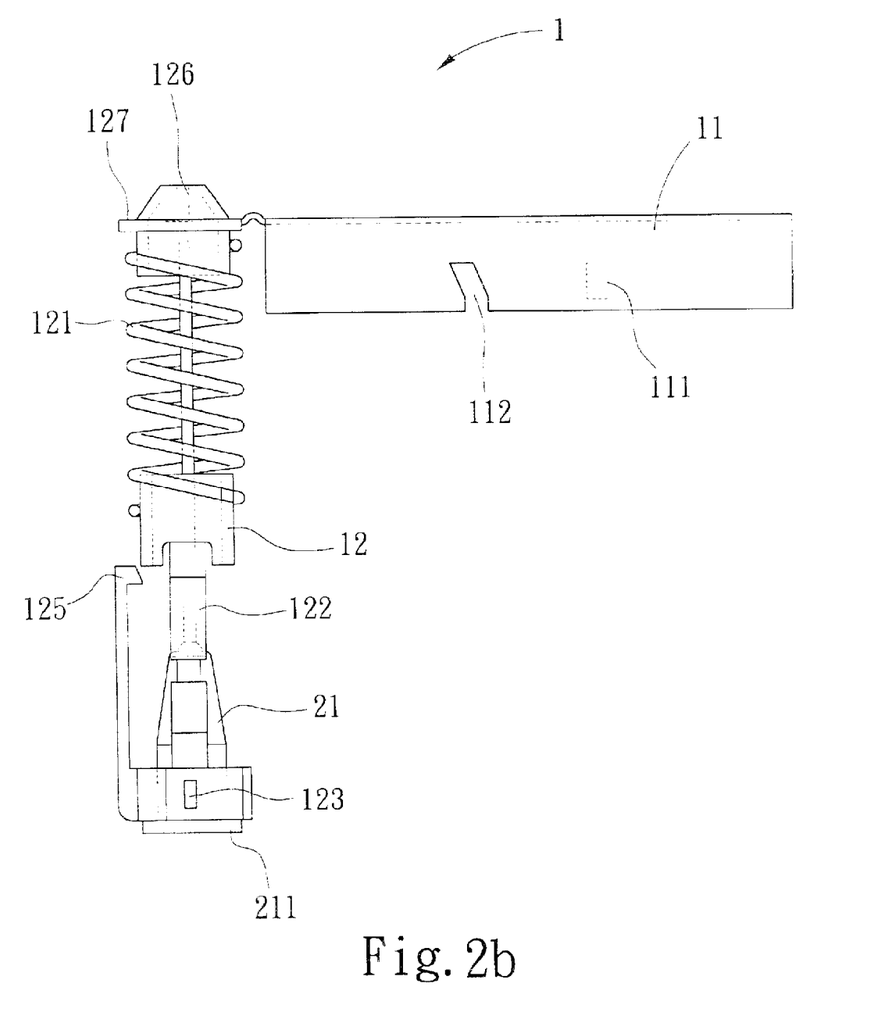
FIG. 2b is a schematic view of the opened protecting sleeve of the embodiment of the present invention.
Figure 3A:
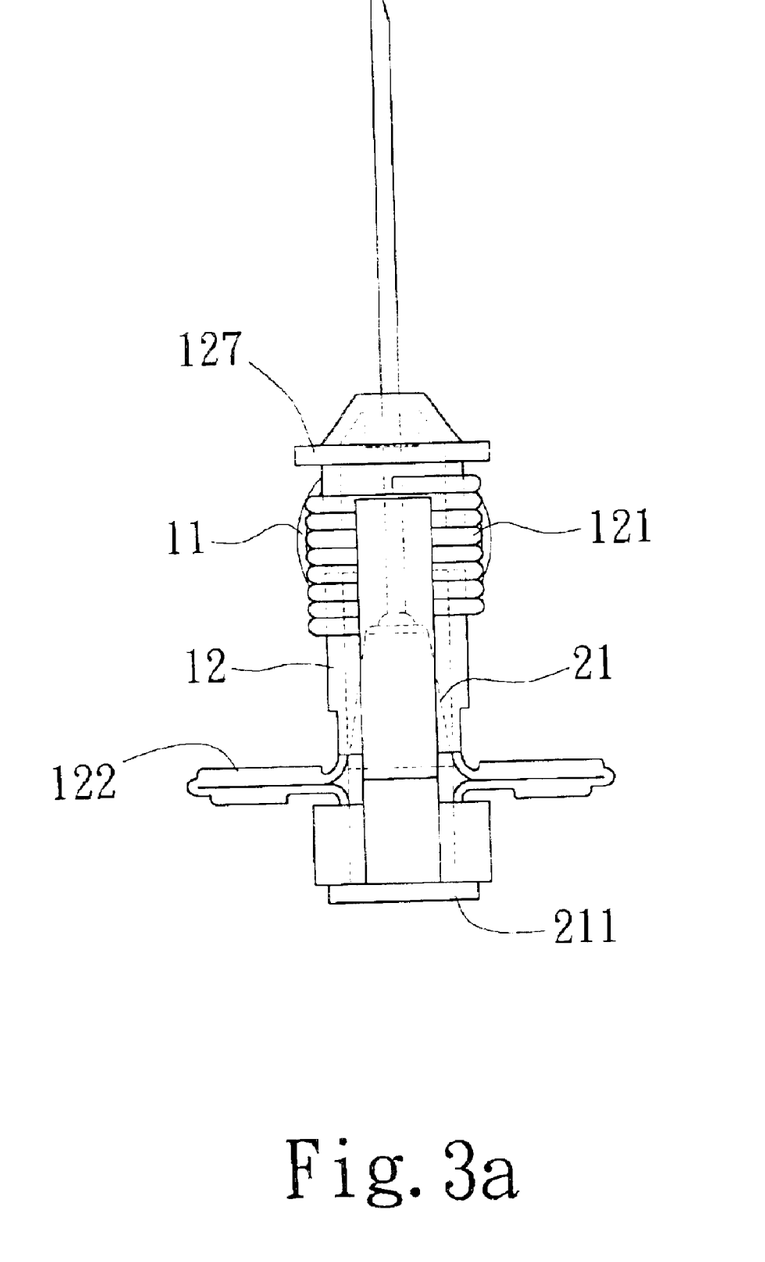
FIG. 3a is a schematic view of the protecting sleeve of the embodiment of the present invention when in compression.
Figure 3B:
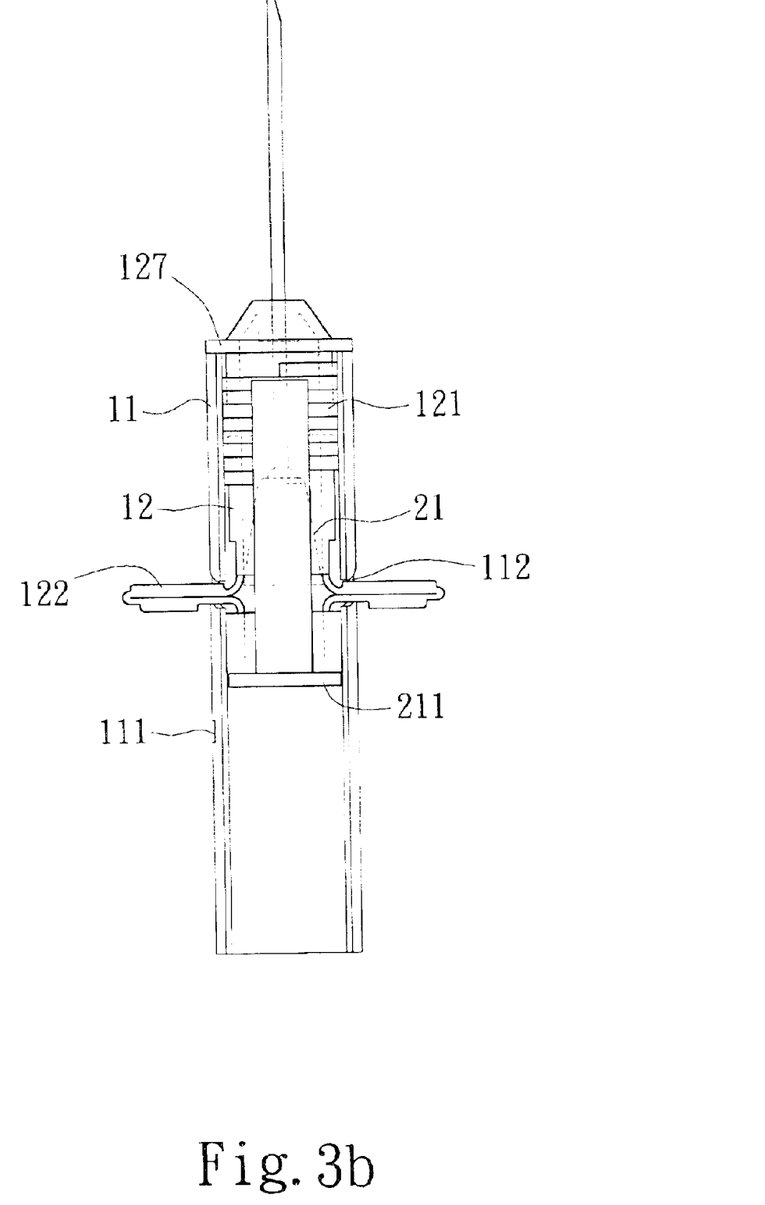
FIG. 3b is a schematic view of the protecting sleeve of the embodiment of the present invention when in compression for engagement.
Figure 4:
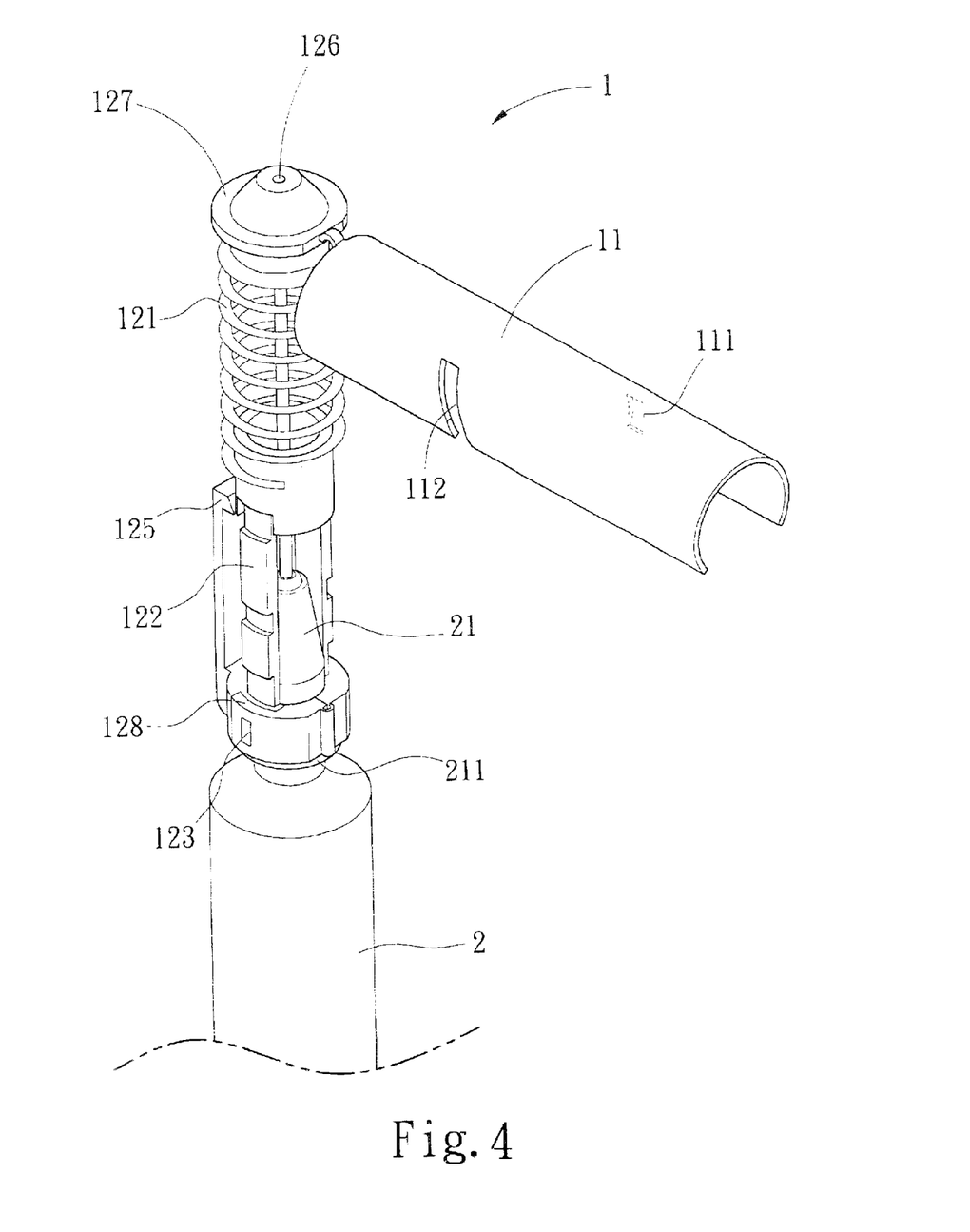
FIG. 4 is a perspective schematic view showing the protecting sleeve of the embodiment of the present invention is connected with a syringe in use.
Figure 5:
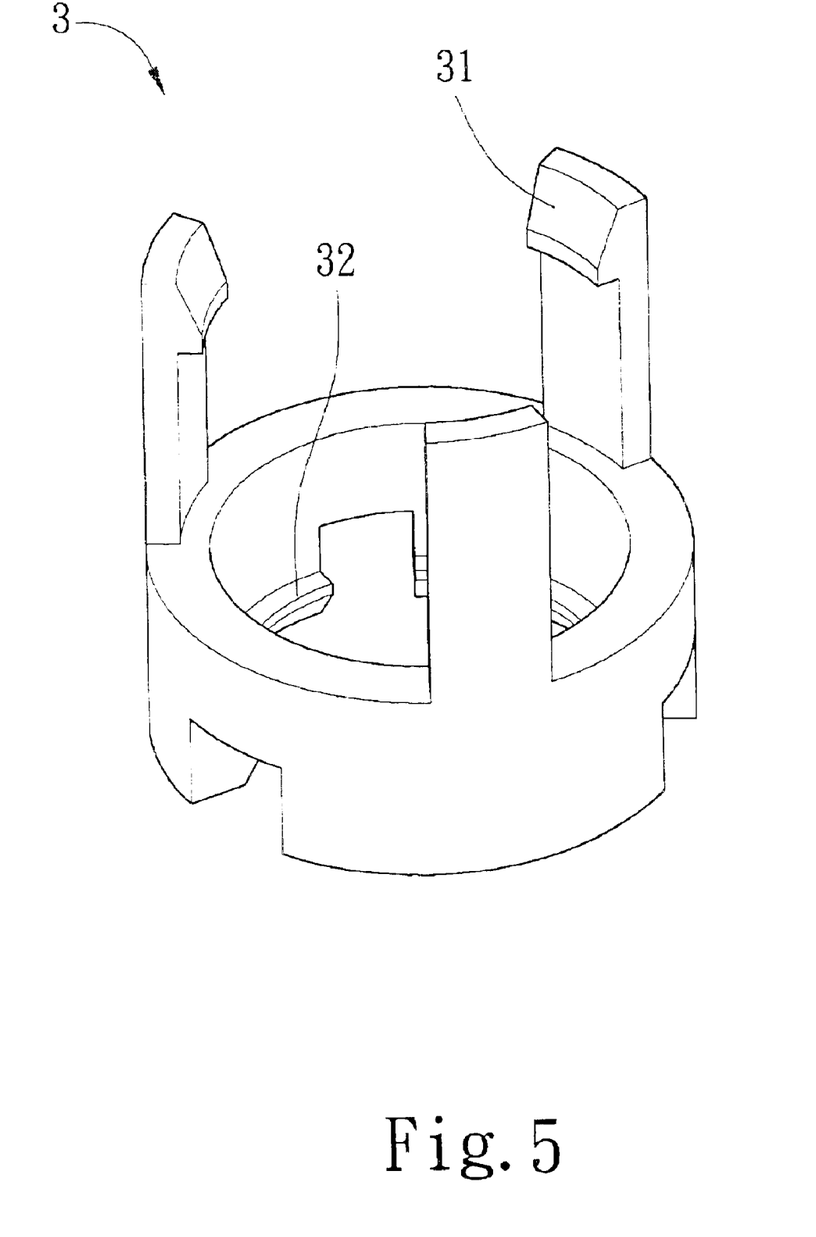
FIG. 5 is a perspective view of a connecting member of the embodiment of the present invention.
Figure 6:
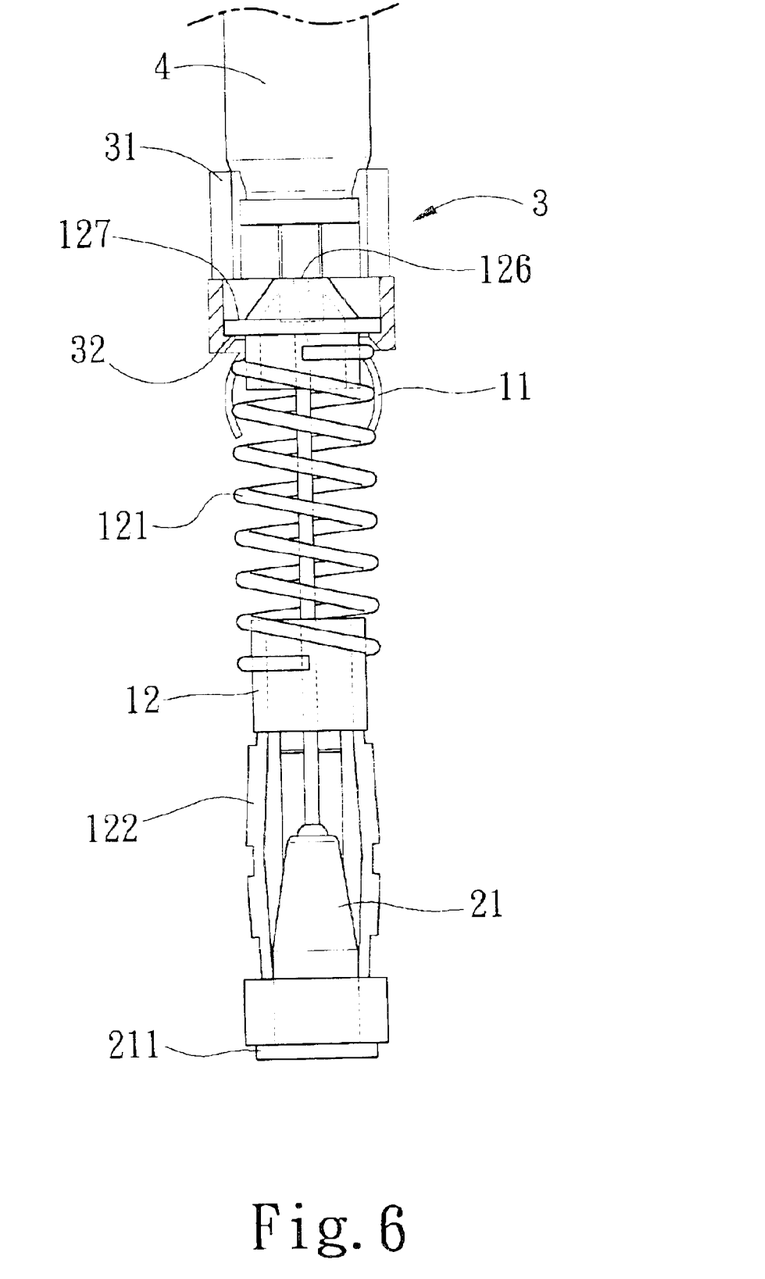
FIG. 6 is a schematic view showing another embodiment of the present invention when in use.

Referring to FIGS. 5, 6, when in medicine injection into a drop bottle, the top end of the cylindrical extendible member 12 of the protecting sleeve 1 is connected with a connecting member 3 on which two ends are provided respectively with three hooks 31 and three hooks 32. The three hooks 32 are mutually engaged with the annular flange 127 provided on the top of the cylindrical extendible member 12; while the other three hooks 31 protruding from the other end of the connecting member 3 can be connected with an injection cap 4, so that during medicine injection, the needle 21 is completely not exposed, this largely increases safety of use.

The present invention thereby has the following advantages:

1. The present invention is designed to make engagement between the cylindrical extendible member and the foldable cover, it can fast envelop the needle to prevent it from accident stabbing; this can largely increase safety of use of the present invention.

2. In the present invention, the cylindrical extendible member can be fixedly engaged with the foldable cover and positioned after being compressed, it is convenient for medicine injection, and thereby, practicality and convenience of the present invention are increased.

In conclusion, the present invention not only can get rid of the defects resided in the conventional syringes, but also can get the objects of fast obscuring the needle, convenience for medicine injection and avoiding accident stabbing of the needle by engagement between the cylindrical extendible member and the foldable cover. Therefore, practicality and convenience of the present invention are largely increased. The present invention can suit various kinds of syringes, thereby, the valued of utility of the present invention can be assured.

Having thus described my invention, what I claim as new and desire to be secured by Letters Patent of the United States are:

1. A protecting cap structure for a needle of a syringe, the protecting cap including a protecting sleeve comprising:

a) a cylindrical member with a hollow interior having:
      i) a compression portion located on first end of the cylindrical member and surrounding the needle; and
      ii) two foldable portions connected to the cylindrical member, the compression portion and the two foldable portions being connected in series, the compression portion and the two foldable portion being moveable between an extended position and a folded position, such that in the extended position the needle is positioned within the hollow interior of the cylindrical member and in the folded position the needle protrudes from the first end of the compression portion;

b) a cover having a semi-circular cross section and pivotally connected to the cylindrical member, the cover selectively locking the compression portion and the foldable portions in one of the extended position and the folded position;

c) a hooking strip extending from a second end of the cylindrical member, and an engaging hole in the cover, wherein the hooking strip engages the engaging hole when the cylindrical member is in the extended position; and d) two engaging notches located on opposing sides of the cover, wherein, when in the folded position, each of the two foldable portions is inserted into one of the two engaging notches.

2. The protecting cap structure according to claim 1, wherein the cylindrical member is integrally made with the cover.

3. The protecting cap structure according to claim 1, wherein the foldable portions are bent outwardly when in the folded position.

4. The protecting cap structure according to claim 1, further comprising a foldable extension member formed on a second end of the cylindrical member adjacent to the two foldable portions, the foldable extension member having a through hole and a protrusion, and being configured to removably lock the needle to the cylindrical member by inserting the protrusion into the through hole.

* * * * *